United States Patent [19]

Smith et al.

[11] Patent Number: 5,031,613
[45] Date of Patent: Jul. 16, 1991

[54] NEBULIZING CATHETER

[75] Inventors: Roy D. Smith, Springfield, Va.;
JoAnne Hahn, 5188 Glen Meadow Dr., Centreville, Va. 22020; Gary Rambadt, 8202 Townsend St., Apt., 20, Fairfax, Va. 22031; Dale Crites, 505 N. Roosevelt Blvd., #304-B, Falls Church, Va. 22044

[73] Assignees: JoAnne Hahn, Centreville; Gary Rambadt, Fairfax; Dale Crites, Falls Church, all of Va.

[21] Appl. No.: 363,172

[22] Filed: Jun. 7, 1989

[51] Int. Cl.⁵ .................. A61M 16/04; A61M 16/10; A61M 11/00
[52] U.S. Cl. ......................... 128/207.14; 128/200.21; 128/207.15; 128/203.12
[58] Field of Search ............. 128/200.14, 200.24, 128/200.26, 203.21, 204.18, 207.14, 207.15, 911, 200.21, 203.12

[56] References Cited

U.S. PATENT DOCUMENTS

| | | | |
|---|---|---|---|
| 3,794,026 | 2/1974 | Jacobs | 128/207.15 |
| 4,155,365 | 5/1979 | Boslau | 128/207.15 |
| 4,444,185 | 4/1984 | Shugar | 128/200.26 |
| 4,449,522 | 5/1984 | Baum | 128/200.26 |
| 4,449,526 | 5/1984 | Elam | 128/207.14 |
| 4,488,548 | 12/1984 | Agdanowski | 128/207.15 |
| 4,497,318 | 2/1985 | Donmichael | 128/207.15 |
| 4,584,998 | 4/1986 | McGrail | 128/207.15 |
| 4,646,733 | 3/1987 | Stroh et al. | 128/207.15 |
| 4,669,463 | 6/1987 | McConnell | 128/207.14 |
| 4,690,138 | 9/1987 | Heyden | 128/207.15 |
| 4,739,756 | 4/1988 | Horn | 128/207.14 |
| 4,892,095 | 1/1990 | Nakhgevany | 128/200.26 |

FOREIGN PATENT DOCUMENTS 0245142 11/1987 European Pat. Off. ....... 128/207.14

Primary Examiner—Edgar S. Burr
Assistant Examiner—Kimberly L. Asher
Attorney, Agent, or Firm—Spencer & Frank

[57] ABSTRACT

A nebulizing catheter and method for delivering a nebulized medication to a patient. The catheter includes an hour-glass shaped neck near its distal end and one or more perforations formed in the distal end. The fluid may be forced through the catheter by a syringe or other suitable means. The catheter is preferably used in conjunction with an endotracheal tube into which the catheter is inserted.

8 Claims, 1 Drawing Sheet

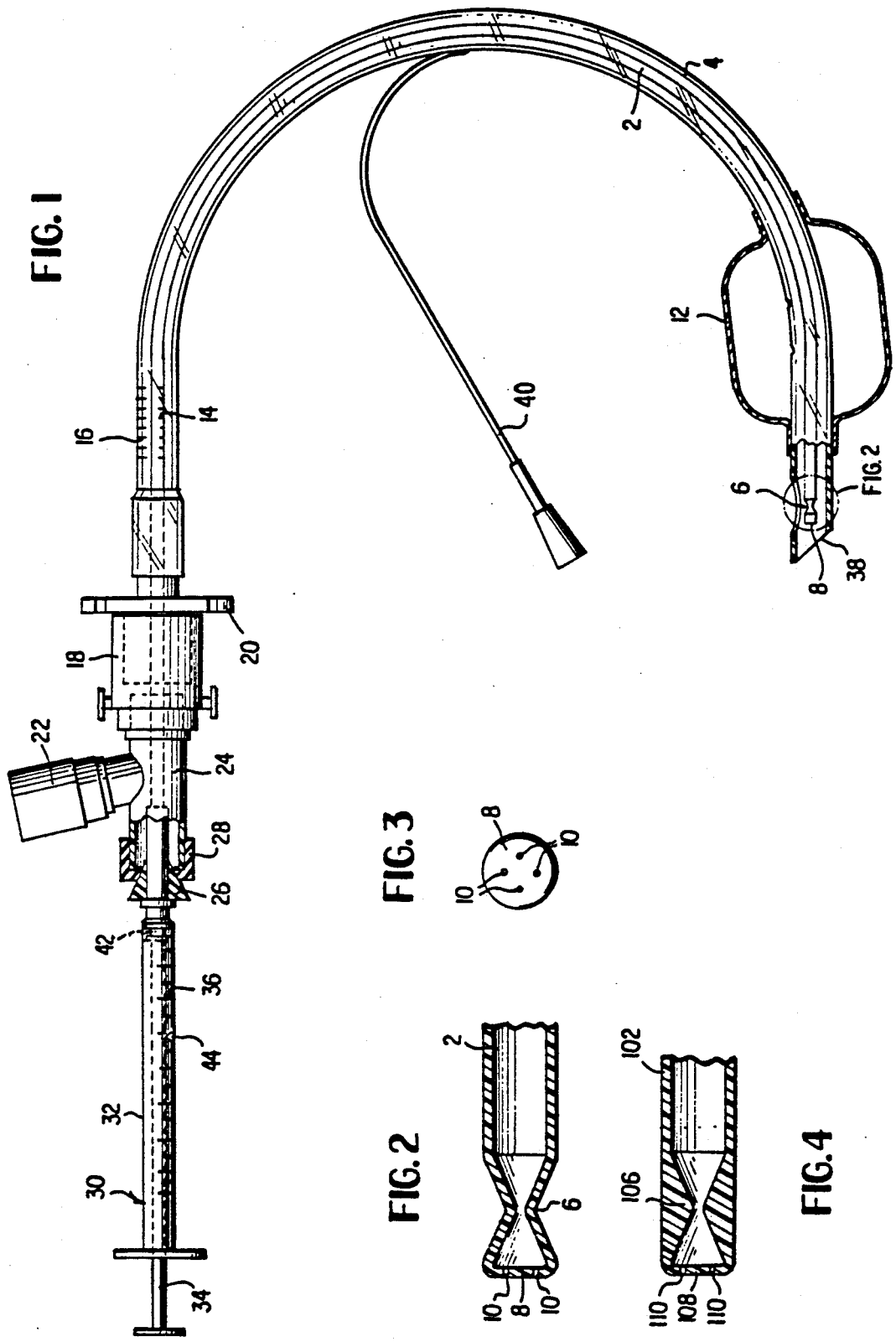

NEBULIZING CATHETER

FIELD OF THE INVENTION

The invention relates to devices and methods for delivering medication to the lungs.

TECHNOLOGY REVIEW

The use of nebulizers with mechanical ventilation devices has been the subject of numerous research articles that have attempted to define the efficacy of delivering a nebulizer treatment "in-line" with mechanical ventilator tubing and/or circuitry to traverse an endotracheal tube. The results of these efforts support a general widespread misconception that the same pattern of aerosol particle deposition is expected to occur with intubated patients, which suggests that indicates the medicine delivered is far less therapeutic.

Modifications of the nebulizer structure and the size of the particles produced, as well as alterations in ventilatory pattern of the mechanical ventilator have been suggested and studied as possible ways of improving aerosol particle deposition into the lung. However, the results are still the same: the endotracheal tube continues to prevent a therapeutic administration of medicine to a patient's lungs.

One attempt to apply medication to the lungs is described in U.S. Pat. No. 4,739,756 to Horn. In Horn a lateral lumen formed in the wall of an endotracheal tube carries medication to a series of orifices formed in the distal end of the endotracheal tube. The orifices are connected to the lumen by a circumferential channel in the tube's distal end. A deficiency of this device is that because of the way the orifices are supplied with medication, laterally along a channel, good uniform nebulization of the mist is difficult to achieve. This is an important drawback, because lung tissue is sensitive and, therefore, large droplets of fluid can damage the lung and induce bronchospasm. Also, because Horn's fluid delivery system is an integral part of the endotracheal tube, the fluid delivery system cannot be removed from the patient's airways for cleaning or for another procedures without removing the entire endotracheal tube. Accordingly, there exists a need for a more simple system of delivering fluid medication as a fine mist to a patient's lungs.

SUMMARY OF THE INVENTION

It is therefore an object of the invention to deliver a nebulizer treatment to patients with whom intubation and/or mechanical ventilation is required to thereby greatly increase the therapeutic effect of the medicine.

The present invention provides a nebulizing catheter and method for delivering a nebulized medication to a patient. The catheter includes an hour-glass shaped neck near its distal end and one or more perforations formed in the distal end. The fluid may be forced through the catheter by a syringe or other suitable means. The catheter is preferably used in conjunction with an endotracheal tube into which the catheter is inserted.

BRIEF DESCRIPTION OF THE DRAWINGS

FIG. 1 shows a elevational view with parts in section of a fluid medication delivery system of one embodiment of the invention including an endotracheal tube and a nebulizing catheter.

FIG. 2 shows an enlarged view of the circled section of FIG. 1.

FIG. 3 shows a end view of the nebulizing catheter of the present invention shown in FIG. 1.

FIG. 4 shows a cross-sectional view of the end of a catheter in an alternative embodiment of the invention

DESCRIPTION OF THE PREFERRED EMBODIMENTS

As seen in FIG. 1, in one embodiment, the invention consists of a hollow plastic catheter 2 having an hourglass shaped neck 6 near its distal end 8. A more detailed view of the end 8 of the catheter 2 can be seen in FIG. 2 which shows perforations 10 that are made in the distal end 8. Preferably the distal end or tip 8 is rounded as shown. The catheter 2 is preferably made of a semi-flexible material suitable for medical devices such as polyvinyl chloride plastic. Typically, the catheter 2 is about 35 to 40 cm in length, but the length used in a given situation varies with the size of the patient. The internal diameter of the catheter 2 is about 3 to 4 mm and the external diameter is about 4 to 5 mm. The catheter wall thickness is typically about 1 mm.

In FIG. 2 the perforations 10 are generally the size of pin pricks, that is less than about 1 mm. While there may be only one perforation 10, preferably, there are several perforations as shown in FIG. 3 which shows the end of the catheter 2. Most preferably, there are at least 3 perforations 10. The perforations 10 are conveniently formed after making the catheter 2 by jabbing pins into the end 8 of the catheter 2, but may also be formed in the process of molding the catheter.

The neck 6 of the catheter 2 may be generally formed in either of two ways. As shown in FIGS. 1 and 2, one way to make a neck 6 is to narrow a section of the catheter by thermo-forming or other means so that the catheter's outer and inner diameter are reduced in the region of the neck 6.

An alternative way to make a neck is shown in FIG. 4. In this embodiment a neck 106 is formed in the process of making a catheter 102 so that only the interior diameter of the catheter 102 is reduced in the region of the neck. As in the previously described embodiment, the catheter 102 has an end 108 with perforations 110.

The narrowest part of the neck 6 is generally about 2 to 3 mm in diameter and about 2 to 3 mm long. The neck 6 is preferably located about 10 mm from the distal end 8 of the catheter 2.

The catheter 2 is preferably used in conjunction with an endotracheal tube 4 as shown in FIG. 1. The endotracheal tube may be provided with an inflatable balloon 12 which is inflated by a lumen 40. The endotracheal tube 4 is typically attached to a connector 18 having a flange 20. The connector 18 in turn is attached to a swivel adaptor 24 having an outlet 22 to a ventilator (not shown).

The catheter 2 is preferably provided with markings 14 which correspond to markings 16 on the endotracheal tube 4. By lining these markings up, it is possible to insert the catheter 2 to the desired extent inside the endotracheal tube 4, generally until the tip 8 of the catheter 2 is almost at the tip 38 of the endotracheal tube 4, preferably less than about 3 mm from the tip of the endotracheal tube 4. Because the tip 38 of the endotracheal tube is typically slanted as shown in FIG. 1, this distance refers to the distance from the tip 8 of the catheter to the slanted edge of the endotracheal tube tip.

A locking mechanism 26 is slid onto or formed as part of the catheter 2. The locking mechanism 26 is preferably made out of rubber so that it can be slid along the catheter 2 and wedged into the a suction port 28 on the swivel adaptor 24 after the catheter has been inserted to a desired extent inside the endotracheal tube 4. Once the locking mechanism is wedged inside the suction port 28, the catheter 2 is prevented from withdrawing or advancing during use.

If the locking mechanism 26 is formed integrally with the catheter 2, it can be located on the catheter 2 at a given position so that the catheter 2 is inserted into the endotracheal tube 4 a set distance before the catheter 2 is locked in place. By using such an integral locking mechanism, a catheter can be produced which can be inserted a desired distance into an endotracheal tube without having to compare the alignment markings on a catheter with the alignment markings on the endotracheal tube.

At the proximal end of the catheter 2 there is a syringe 30 having an barrel section 32 and a plunger 34. The syringe 30 may be formed either integrally with the catheter 2 or be attached later. The syringe barrel 32 is provided with markings 36 to indicate the quantity of air to be displaced into the catheter 2.

The design of the invention allows it to provide medicinal aerosol particles which are inhaled into the lungs either spontaneously or in conjunction with mechanical ventilator breathing.

The catheter 2 can be prefilled with a known amount of drug or diluent, which is then displaced towards the tip 8 of the catheter by the syringe 30. As the plunger 34 is pulled back, air enters the syringe 30. This air is then displaced into the the barrel 32 and pressure is thereby exerted on the fluid in the catheter 2 when the plunger 34 is pressed into the barrel 32. By repeatedly pressing in the syringe plunger 34 a set amount, intermittant nebulization and complete dispersion of the contents of the catheter is achieved. A preferred dosage of fluid injected at one time is about 0.05 cc, but this quantity may vary somewhat with the size of the catheter and the medication used. To ensure that the proper amount of air is drawn into the syringe barrel 32, a stop 44 may be provided in the barrel 32 which prevents the plunger 34 from being accidently pulled back too far. The stop 44 does this by releasably engaging the tip 4 of the plunger 34 as the plunger 34 is pulled back.

Because the catheter 2 is separate from the endotracheal tube 4, the catheter 2 may be removed from the endotracheal tube 4 when no more nebulization is needed so that other devices may be inserted into the endotracheal tube.

By varying the size of the nebulizer system, particularly the filled catheter, the system may be used for any size patient, including pediatric and neonatal patients.

Further, because of the invention's improved system for delivering nebulized particles to the lungs, less medication is needed to produce an effective therapeutic response.

Also, because the system is disposable, it less subject to cross-contamination than are current systems for providing nebulized medicine.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A device for delivering a nebulized medication to a patient comprising an endotracheal tube having inserted therein a catheter having a distal end and means for nebulizing a fluid medication which is forced through said catheter including an hour-glass shaped neck near the distal end of said catheter and at least one perforation in said distal end which allows fluid to exit said catheter as a fine mist, said catheter contained within said endotracheal tube so that said fine mist is adapted to be delivered to a patient after exiting said catheter.

2. The device of claim 1 further comprising a syringe means for forcing said fluid through said catheter.

3. The device of claim 1 further comprising means on said endotracheal tube and said catheter for indicating how far said catheter has been inserted into said endotracheal tube.

4. The device of claim 1 wherein said endotracheal tube includes an external inflatable balloon and means for inflating said balloon.

5. The device of claim 1 wherein said distal end of said catheter is no more than about 3 mm from the distal end of said endotracheal tube.

6. The device of claim 1 further comprising means for locking said catheter in place relative to said endotracheal tube.

7. A method for delivering a nebulized medication to a patient comprising the steps of:
   inserting a catheter inside an endotracheal tube;
   forcing a fluid medication through said catheter;
   nebulizing said fluid by means of an hour-glass shaped neck near the distal end of said catheter and at least one perforation in said distal end; and
   allowing said nebulized fluid to exit said catheter as a fine mist.

8. The method of claim 7 wherein about 0.05 cc of fluid are forced through said catheter.

* * * * *